US012734474B2

(12) United States Patent
Furue et al.

(10) Patent No.: US 12,734,474 B2
(45) Date of Patent: Sep. 15, 2026

(54) GAS SEPARATION SYSTEM AND METHOD FOR PRODUCING METHANE-ENRICHED GAS

(71) Applicant: UBE Corporation, Ube (JP)

(72) Inventors: Kensuke Furue, Ube (JP); Shota Kitai, Ube (JP); Takumi Fukunaga, Ube (JP); Nobuhiko Fukuda, Ube (JP); Tomohide Nakamura, Ube (JP)

(73) Assignee: UBE Corporation, Ube (JP)

( * ) Notice: Subject to any disclaimer, the term of this patent is extended or adjusted under 35 U.S.C. 154(b) by 0 days.

(21) Appl. No.: 18/998,309

(22) PCT Filed: Jan. 17, 2024

(86) PCT No.: PCT/JP2024/001095
§ 371 (c)(1),
(2) Date: Jan. 24, 2025

(87) PCT Pub. No.: WO2025/154196
PCT Pub. Date: Jul. 24, 2025

(65) Prior Publication Data
US 2026/0008003 A1 Jan. 8, 2026

(51) Int. Cl.
*B01D 53/22* (2006.01)
*C07C 7/00* (2006.01)
(Continued)

(52) U.S. Cl.
CPC ......... *B01D 53/226* (2013.01); *B01D 53/227* (2013.01); *C07C 7/005* (2013.01);
(Continued)

(58) Field of Classification Search
None
See application file for complete search history.

(56) References Cited

U.S. PATENT DOCUMENTS

2017/0304769 A1 10/2017 Bigeard et al.
2018/0272272 A1 9/2018 Hasegawa et al.
(Continued)

FOREIGN PATENT DOCUMENTS

EP 0700709 A1 * 3/1996 ......... C01B 21/0438
JP 2013-128868 A 7/2013
(Continued)

OTHER PUBLICATIONS

EP0700709A1_ENG (Espacenet machine translation of Willemot) (Year: 1996).*

*Primary Examiner* — Gabriel E Gitman
(74) *Attorney, Agent, or Firm* — KNOBBE, MARTENS, OLSON & BEAR, LLP

(57) ABSTRACT

A gas separation system for producing a $CH_4$-enriched gas from a feedstock gas containing $CO_2$ and $CH_4$, including a first gas separation membrane unit and a second gas separation membrane unit, in which the gas separation system includes a feedstock gas supply line connected to a gas inlet of the first gas separation membrane unit; a compression part disposed in the feedstock gas supply line; a first line connecting the retentate gas outlet of the first gas separation membrane unit and the gas inlet of the second gas separation membrane unit; a second line connecting the permeate gas outlet of the second gas separation membrane unit and the feedstock gas supply line; and a cooling part for lowering the operating temperature of the second gas separation membrane unit below the operating temperature of the first gas separation membrane unit.

14 Claims, 2 Drawing Sheets

(51) Int. Cl.
*C07C 7/144* (2006.01)
*C10L 3/10* (2006.01)

(52) U.S. Cl.
CPC .............. *C07C 7/144* (2013.01); *C10L 3/104* (2013.01); *B01D 2053/224* (2013.01); *B01D 2256/245* (2013.01); *B01D 2257/504* (2013.01); *B01D 2258/05* (2013.01)

(56) References Cited

U.S. PATENT DOCUMENTS

| | | | | |
|---|---|---|---|---|
| 2019/0046922 | A1* | 2/2019 | Jensvold | B01D 53/226 |
| 2022/0184549 | A1 | 6/2022 | Nakamura et al. | |
| 2022/0184550 | A1* | 6/2022 | Liu | B01D 69/125 |
| 2022/0203295 | A1* | 6/2022 | Myrick | B01D 53/225 |
| 2025/0136884 | A1* | 5/2025 | O'Brien | B01D 53/226 |

FOREIGN PATENT DOCUMENTS

| | | | |
|---|---|---|---|
| JP | 2014-117687 | A | 6/2014 |
| JP | 2016-187769 | A | 11/2016 |
| JP | 2020-163282 | A | 10/2020 |
| WO | WO 2017/056135 | A1 | 4/2017 |
| WO | WO 2020/203994 | A1 | 10/2020 |

* cited by examiner 10 17 18 53 11c 22 12c 50 11b 12b 26 21 23 24 25 11a 11 14 12a 12 15

40 35 39 36 38 32 37 33 31 30 34 32 Y

GAS SEPARATION SYSTEM AND METHOD FOR PRODUCING METHANE-ENRICHED GAS

CROSS-REFERENCE TO RELATED APPLICATIONS

This application is the U.S. National Phase under 35 U.S.C. § 371 of International Application PCT/JP2024/001095, filed Jan. 17, 2024, the entire content of which is incorporated herein by reference.

TECHNICAL FIELD

The present invention relates to a gas separation system for separating a mixed gas containing $CO_2$ and methane ($CH_4$) using a plurality of gas separation membrane units, and a method for producing a $CH_4$-enriched gas using the same.

BACKGROUND ART

As a method for separating a mixed gas containing two or more kinds of gases into respective gases, there is known a membrane separation method based on the difference between the gas permeation rates of the gases through a membrane. In this method, a target gas or target gases (specifically, a gas that has high purity and easily permeates the membrane and/or a gas that has high purity and does not easily permeate the membrane) can be obtained by collecting the permeate gas and/or the retentate gas (hereinafter, the gas that easily permeates a membrane and the gas that does not easily permeate a membrane are also referred to as "easily permeating gas" and "non-easily permeating gas", respectively). For each gas included in a mixed gas, the gas permeation rate of a membrane can be represented by P' (unit: $\times 10^{-5}$ $cm^3(STP)/cm^2 \cdot sec \cdot cmHg$), which is the volume of the gas passing through the membrane, per unit membrane area, unit time, and unit partial pressure difference. The gas separation selectivity of the membrane can be defined as a ratio "easily permeating gas permeation rate/non-easily permeating gas permeation rate".

In general, a gas separation membrane having a high gas separation selectivity has a low gas permeation rate, whereas a membrane having a high gas permeation rate has a low gas separation selectivity. Therefore, in the case where the non-easily permeating gas with a certain purity is recovered from the mixed gas using the single-stage gas separation membrane, the recovery rate is higher when the membrane having high gas separation selectivity is used; however, due to the low permeation rate, it is necessary to increase the membrane area or to increase the operating pressure. On the other hand, in the case of a membrane having a high permeation rate, it is not necessary to increase the membrane area or the operating pressure, but the recovery rate is low because of the low gas separation selectivity.

In general, a gas separation membrane having gas permselectivity is used in the form of a gas separation membrane module, which includes: a housing having at least a gas inlet, a permeate gas outlet, and a retentate gas outlet; and the gas separation membrane packed therein. The gas separation membrane is set in the housing such that the space on the gas supply side is isolated from the space on the side the gas having passed through the membrane reaches. In order to obtain a required membrane area, a plurality of such gas separation membrane modules are generally combined in parallel to form a gas separation membrane unit, which is used in a gas separation system. Since the plurality of gas separation membrane modules constituting the gas separation membrane unit share a gas inlet, a retentate gas outlet, and a permeate gas outlet, the gas separation membrane unit substantially acts as a large gas separation membrane module.

There is known a method involving use of a system including such gas separation membrane units in multiple stages to recover a target non-easily permeating gas at a high purity and a high recovery rate. Examples of the multistage gas separation system include a system that further subjects the first-stage retentate gas enriched in the non-easily permeating gas to separation to improve the purity, and a system that recovers the non-easily permeating gas contained in the first-stage permeate gas to improve the recovery rate.

There is known a method for producing a $CH_4$-enriched gas from a feedstock gas containing $CO_2$ and $CH_4$ by membrane separation using a plurality of gas separation membrane units (for example, Patent Literature 1). Patent Literature 1 describes the separation of biogas cooled to 0 to −60° C. into $CH_4$ and $CO_2$.

CITATION LIST

Patent Literature

Patent Literature 1: US2017/0304769A1

SUMMARY OF INVENTION

However, the gas separation system described in Patent Literature 1 is not sufficient for obtaining high purity $CH_4$ gas at low cost using separation membrane with a small area.

The present invention solves the above problems. The present invention provides the following.

[1] A gas separation system for producing a $CH_4$-enriched gas from a feedstock gas comprising $CO_2$ and $CH_4$,
the gas separation system comprising a first gas separation membrane unit and a second gas separation membrane unit, wherein
each of the first gas separation membrane unit and the second gas separation membrane unit includes at least a gas inlet, a permeate gas outlet and a retentate gas outlet, and
the gas separation system comprises:
a feedstock gas supply line connected to the gas inlet of the first gas separation membrane unit;
a compression part disposed in the feedstock gas supply line;
a first line connecting the retentate gas outlet of the first gas separation membrane unit and the gas inlet of the second gas separation membrane unit;
a second line connecting the permeate gas outlet of the second gas separation membrane unit and the feedstock gas supply line, and
a cooling part for lowering an operating temperature of the second gas separation membrane unit, T2, below an operating temperature of the first gas separation membrane unit, T1.

[2] The gas separation system as set forth in [1], wherein a gas permeation rate of the second gas separation membrane unit at 40° C., $P_2'CO_2^{(40)}$, is higher than a gas permeation rate of the first gas separation membrane unit at 40° C., $P_1'CO_2^{(40)}$.

[3] The gas separation system as set forth in [1] or [2], wherein a carbon dioxide gas permeation rate of the second gas separation membrane unit at the operating temperature T2, $P_1'CO_2^{(T2)}$, is larger than a carbon dioxide gas permeation rate of the first gas separation membrane unit at the operating temperature T1, $P_1'CO_2^{(T1)}$.

[4] The gas separation system as set forth in any one of [1] to [3], wherein a temperature of a gas supplied to the second gas separation membrane unit, t2, is 30° C. or less.

[5] The gas separation system as set forth in any one of [1] to [4], wherein a temperature of the gas supplied to the second gas separation membrane unit, t2, is lower than a temperature of a gas supplied to the first gas separation membrane unit, t1.

[6] The gas separation system as set forth in any one of [1] to [5], wherein a difference between the operating temperatures T1 and T2, T1-T2, is 10° C. or more.

[7] The gas separation system as set forth in any one of [1] to [6], comprising a heating part for heating the feedstock gas supplied to the first gas separation membrane unit, the heating part being provided in the feedstock gas supply line.

[8] The gas separation system as set forth in any one of [1] to [7], wherein during operation of the gas separation system, a gas separation membrane included in the second gas separation membrane unit has a separation selectivity $P_2'CO_2/P_2'CH_4$ of 15 or more and 3000 or less, and a $CO_2$ permeation rate P2'CO2 of $3\times10^{-5}$ $cm^3$ (STP)/$cm^2$·sec·cmHg or more and $80\times10^{-5}$ $cm^3$ (STP)/$cm^2$·sec·cmHg or less.

[9] The gas separation system as set forth in any one of [1] to [8], wherein the cooling part is disposed in the first line.

[10] The gas separation system as set forth in any one of [1] to [9], wherein a proportion of an amount of a gas flow refluxed to the first gas separation membrane unit in an amount of a gas flow supplied to the first gas separation membrane unit is 10 to 60%.

[11] The gas separation system as set forth in any one of [1] to [10], further comprising a third gas separation membrane unit, wherein the third gas separation membrane unit comprises at least a gas inlet, a permeate gas outlet and a retentate gas outlet, and the gas separation system comprises:

a third line connecting the permeate gas outlet of the first gas separation membrane unit and the gas inlet of the third gas separation membrane unit, and a fourth line connecting the retentate gas outlet of the third gas separation membrane unit and the feedstock gas supply line.

[12] The gas separation system as set forth in [11], wherein the operating temperature of the second gas separation membrane unit is lower than an operating temperature of the third gas separation membrane unit.

[13] The gas separation system as set forth in any one of [1] to [12], comprising a liquefaction device for further cooling and liquefying a retentate gas of the second gas separation membrane unit.

[14] The gas separation system as set forth in any one of [1] to [13], wherein a cooled retentate gas of the second gas separation membrane unit is used to lower the operating temperature of the second gas separation membrane unit.

[15] A method for producing a $CH_4$-enriched gas, comprising supplying a feedstock gas comprising at least $CO_2$ and $CH_4$ to a gas separation system, wherein the gas separation system comprises at least a first gas separation membrane unit and a second gas separation membrane unit, each of the first gas separation membrane unit and the second gas separation membrane unit includes at least a gas inlet, a permeate gas outlet, and a retentate gas outlet, and the gas separation system comprises:

a feedstock gas supply line connected to the gas inlet of the first gas separation membrane unit;

a compression part disposed in the feedstock gas supply line:

a first line connecting the retentate gas outlet of the first gas separation membrane unit and the gas inlet of the second gas separation membrane unit;

a second line connecting the permeate gas outlet of the second gas separation membrane unit and the feedstock gas supply line, and a cooling part for lowering an operating temperature of the second gas separation membrane unit below an operating temperature of the first gas separation membrane unit.

DESCRIPTION OF EMBODIMENTS

The present invention will be described below based on preferred embodiments thereof with reference to the drawings.

Any upper limits and any lower limits for the numerical values disclosed herein can be combined without any limitation.

Each of the gas separation systems shown in FIGS. 1 and 3 to 5 includes a first gas separation membrane unit 11 and a second gas separation membrane unit 12. Each of the gas separation systems shown in FIGS. 3 and 5 further includes a third gas separation membrane unit 13.

Figures 1, 2, 3:
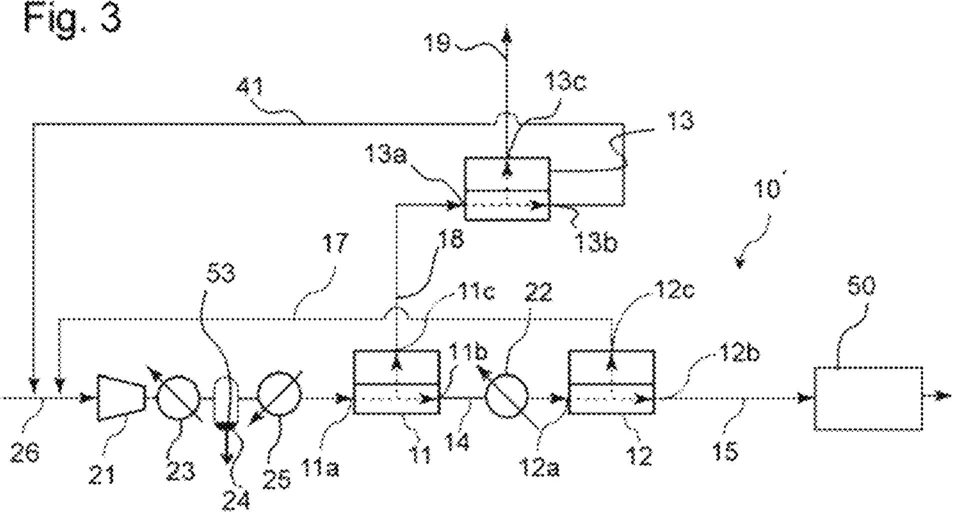
FIG. 1 is a schematic diagram showing a configuration of a gas separation system according to the first embodiment of the present invention.
FIG. 2 is a schematic view showing a structure of an exemplary gas separation membrane module used in the gas separation system of the present invention.
FIG. 3 is a schematic diagram showing a configuration of a gas separation system according to the second embodiment of the present invention.

For each of the gas separation membrane units 11, 12, and 13, for example, a module 40 including a casing 31 and a gas separation membrane 30 housed therein, as shown in FIG. 2, can be used, the gas separation membrane 30 being composed of hollow fiber membranes or the like and having gas permselectivity. Each of the gas separation membrane units 11, 12, and 13 shown in FIGS. 1 and 3 may be a single gas separation membrane module 40 shown in FIG. 2, or may be composed of a plurality of the modules 40 arranged in parallel, for example. Two opposing sides of the casing 31 of the module 40 are opened to form an opening 32. It should be noted that the opening 32 is for inserting the gas separation membrane 30 into the casing 31, and is not an opening of the gas separation membrane 30. The gas separation membrane 30 is housed in the casing 31 through the opening 32. In the case where the gas separation membrane 30 includes a hollow fiber membrane bundle, the gas separation membrane 30 is housed in the casing 31 such that the end portion of each hollow fiber membrane is open in the vicinity of each opening 32 of the casing 31 in the housed state.

In a state where the gas separation membrane 30 is housed in the casing 31, the gas separation membrane 30 is fixed to the inner wall of the casing 31 by tube plates 33 and 34 at positions of both end portions in the Y direction, which is the extending direction of the hollow fiber membrane. Each opening 32 of the casing 31 is closed by lids 35 and 36. The lid 35 has a gas inlet 37. On the other hand, the lid 36 has a retentate gas outlet 38. The mixed gas to be subjected to separation is introduced into the module from the gas inlet 37 of the lid 35. Of the introduced gas, the gas that has permeated the gas separation membrane 30 is discharged to the outside of the module through a permeate gas outlet 39 of the casing 31. On the other hand, the retentate gas, which has not permeated the gas separation membrane 30, is discharged from the retentate gas outlet 38 of the lid 36 to the outside of the module. In some cases, a purge gas supply port (not shown) may be provided in the casing 31. Although the separation membrane module of FIG. 2 has been described as an example, the present invention can be applied to separation membrane modules having other configurations, and can be applied to, for example, a shell feed type module.

Returning to FIG. 1, the first gas separation membrane unit 11 and the second gas separation membrane unit 12 are connected in series, as shown in FIG. 1. Specifically, the first gas separation membrane unit 11 and the second gas separation membrane unit 12 are connected by connecting the retentate gas outlet 11*b* of the first gas separation membrane unit 11 and the gas inlet 12*a* of the second gas separation membrane unit 12 by the first line 14.

Hereinafter, the gas inlets, the outlets, the supplied gases, the permeate gases, and the retentate gases of the first gas separation membrane unit 11 and the second gas separation membrane unit 12 may be mentioned with the terms "first" and "second", respectively. The same applies to the third gas separation membrane unit 13 described later. Further, "upstream" and "downstream" hereinafter described are based on the flow direction of the feedstock gas.

In each gas separation membrane unit in the system 10. $CO_2$ is a gas having a high gas permeation rate through the gas separation membrane, that is, an easily permeating gas, and $CH_4$ is a gas having a low gas permeation rate through the gas separation membrane, that is, a non-easily permeating gas.

A feedstock gas supply line 26 for supplying a feedstock gas from a feedstock gas source (not shown) to the first gas separation membrane unit 11 is connected to the first gas inlet 11*a* of the first gas separation membrane unit 11. A compression part 21 is disposed in the middle of the feedstock gas supply line 26.

The permeate gas outlet 12*c* of the second gas separation membrane unit 12 is connected to a feedstock gas supply line 26 by a second line 17. Specifically, the second line 17 is connected to the second permeate gas outlet 12*c* and also to the feedstock gas supply line 26 at a position on the suction side of the compression part 21.

The compression part 21 is provided for the purpose of pressurizing the feedstock gas supplied from the feedstock gas source, and also for the purpose of pressurizing the second permeate gas discharged from the second gas separation membrane unit 12 when the permeate gas is returned to the first gas separation membrane unit 11 through the second line 17. As the compression part 21, the same part as those used so far in the technical field can be used. For example, a compressor can be used. When the feedstock gas is supplied to the system, the feedstock gas usually contains about 0 to 10% by mass of moisture.

A recovery line 15 for taking out the retentate gas, specifically, a $CH_4$-enriched gas, is connected to the retentate gas outlet 12*b* of the second gas separation membrane unit 12. In the recovery line 15, a liquefaction part 50 for liquefying the $CH_4$ gas ($CH_4$-enriched gas) discharged from the second retentate gas outlet 12*b* may be provided on the downstream side of the retentate gas outlet 12*b*. As $CH_4$ gas for producing liquefied methane, high purity methane having an impurity concentration reduced to about several ten ppmv is required according to the standard, and the present invention can achieve such purity at low cost.

A cooling unit 23 capable of cooling the feedstock gas compressed by the compression unit 21 is provided downstream of the compression unit 21 in the feedstock gas flow direction in the feedstock gas supply line 26. Further, a condensed flow line 24 and a heating part 25 are provided downstream of the cooling part 23. The condensed flow line 24 is for separating and removing a condensed flow of moisture or the like generated by cooling by the cooling part from the feedstock gas supply line 26, and the beating part 25 is for heating the feedstock gas after separation of the condensed flow to a desired temperature. As the cooling part 23, a conventionally known part can be used, such as a heat exchanger. As the heating part 25, a conventionally known heater can be used.

The system 10 is characterized in that a cooling unit 22 is provided to lower the operating temperature of the second gas separation membrane unit 12 below the operating temperature of the first gas separation membrane unit 11. Here, the operating temperature refers to the temperature of the gas separation membrane of the corresponding gas separation membrane unit. The cooling unit 22 may directly cool the gas separation membrane of the second gas separation membrane unit 12, or may cool the retentate gas of the first gas separation membrane unit 11 supplied to the second gas separation membrane unit 12 (second supply gas) to thereby cool the gas separation membrane.

In the present embodiment, the cooling part 22 is disposed in the first line 14 to cool the second supply gas.

As the gas separation membranes of the gas separation membrane modules of the first gas separation membrane unit 11 and the second gas separation membrane unit 12, gas separation membranes made of a polymer material are used, for example. The gas separation membrane used can be, for example, a flat membrane in the form of a film, or a hollow fiber membrane in the form of a hollow fiber. In particular, it is preferable to use a hollow fiber membrane element obtained by bundling a plurality of hollow fiber membranes as the gas separation membrane, in view of increasing the throughput.

As the polymer material of the gas separation membrane, a material having a permselectivity for $CO_2$ compared to $CH_4$ is preferably used. Such polymer materials include glassy polymer materials or rubbery polymer materials. Examples of the glassy polymer material include polyimide, polyamide, polyamideimide, cellulosic materials such as cellulose acetate, polysulfone, polyethersulfone, polyphenylsulfone, and polycarbonate. Examples of the rubbery polymer material include a silicone resin and a polybutadiene resin.

In particular, it is preferable to use polyimide for the gas separation membrane of the second gas separation film unit 12, in view of highly exhibiting the effect of the present invention.

Polyimide is also preferably used as a material of the gas separation membrane of the first gas separation membrane unit 11 and that of the third gas separation membrane unit 13 described later.

When polyimide is used for the gas separation membrane, it can be obtained by synthesizing a polyamic acid by using a tetracarboxylic acid component and a diamine component, and dehydrating/imidizing the polyamic acid by heat treatment.

As the tetracarboxylic acid component, aliphatic tetracarboxylic dianhydride or aromatic tetracarboxylic dianhydride can be used. As the diamine component, aliphatic diamine or aromatic diamine can be used.

Examples of the aliphatic tetracarboxylic dianhydrides include cyclobutane-1,2,3,4-tetracarboxylic dianhydride, 1,2,4,5-cyclohexanetetracarboxylic dianhydride, dicyclohexyl-3,3',4,4'-tetracarboxylic dianhydride, 1,2,4,5-cyclohexanetetracarboxylic-1,2:4,5-dianhydride, 1,2,3,4-cyclobutanetetracarboxylic dianhydride, bicyclo[2.2.2]oct-7-ene-2,3; and 5,6-tetracarboxylic dianhydride.

The aromatic tetracarboxylic dianhydride preferably has 2 to 3 aromatic rings, and examples include 3,3',4,4'-biphenyltetracarboxylic dianhydride, 4,4'-(hexafluoroisopropylidene)-bis(phthalic anhydride) (this compound is also referred to as 2,2-bis(3,4-dicarboxyphenyl)hexafluoropropane dianhydride), 2,3,3',4'-biphenyltetracarboxylic dianhydride, 2,2',3,3'-biphenyltetracarboxylic dianhydride, pyromellitic dianhydride, benzophenonetetracarboxylic dianhydride, 4,4'-oxydiphthalic dianhydride, diphenylsulfonetetracarboxylic dianhydride, p-terphenyltetracarboxylic dianhydride, and m-terphenyltetracarboxylic dianhydride.

Examples of the aliphatic diamine include trans-1,4-diaminocyclohexane, cis-1,4-diaminocyclohexane, 1,6-hexamethylenediamine, 1,10-decamethylenediamine, 1,3-bis(aminomethyl)cyclohexane, 1,4-bis(aminomethyl)cyclohexane, and polyoxypropylenediamine having a weight average molecular weight of 500 or less.

Examples of the aromatic diamines include paraphenylenediamine, metaphenylenediamine, 4,4'-oxydianiline, 3,4'-oxydianiline, 4,4'-diaminodiphenylmethane, 2,4-toluenediamine, 3,3'-dihydroxy-4,4'-diaminobiphenyl, bis(4-amino-3-carboxyphenyl)methane, 2,4-diaminotoluene, and 3,5-diaminobenzoic acid, 3,7-diamino-2,8-dimethyldibenzothiophene=5,5-dioxide as main component with isomers 3,7-diamino-2,6-dimethyldibenzothiophene=5,5-dioxide and 3,7-diamino-4,6-dimethyldibenzothiophene=5,5-dioxide, which have a methyl group at a different position, 2,2',5,5'-tetrachlorobenzidine, 3,3',5,5'-tetrachlorobenzidine, 3,3'-dichlorobenzidine, 2,2'-dichlorobenzidine, 2,2',3,3',5,5'-hexachlorobenzidine, 2,2',5,5'-tetrabromobenzidine, 3,3',5,5'-tetrabromobenzidine, 3,3'-dibromobenzidine, 2,2'-dibromobenzidine, 2,2',3,3',5,5'-hexachlorobenzidine, 3,3'-diaminodiphenylsulfone, 3,3'-diamino-4,4'-dimethyl-diphenylsulfone, and 3,3'-diamino-4,4'-diethyl-diphenylsulfone.

In the present invention, when polyimide is used as the material of the gas separation membrane of the second gas separation membrane unit 12, aromatic polyimide may be used in particular. The aromatic polyimide can be obtained by using an aromatic tetracarboxylic acid component and an aromatic diamine component.

In the present invention, when polyimide is used as the material of the gas separation membrane of the first gas separation membrane unit 11 and the third gas separation membrane unit 13 described later, aromatic polyimide may be used.

When a gas separation membrane made of polyimide is used for each of the first gas separation membrane unit 11, the second gas separation membrane unit 12, and the third gas separation membrane unit 13, an asymmetric membrane may be used as the gas separation membrane. The asymmetric membrane generally has a two-layer structure composed of a dense skin layer for separating a target gas and a porous layer for supporting the skin layer.

As the gas separation membranes of each of the first gas separation membrane unit 11, the second gas separation membrane unit 12, and the third gas separation membrane unit 13, those particularly suitably used are hollow fiber gas separation membranes of polyimide having an asymmetric structure composed of the skin layer with a thickness of 10 nm or more and 200 nm or less and the porous layer with a thickness of 20 μm or more and 200 μm or less, and also having an inner diameter of about 30 μm or more and 500 μm or less.

The operation of the gas separation system 10 of the present embodiment having the above-described configuration will be described. The feedstock gas containing $CH_4$ and $CO_2$, which are targets for separation, is supplied from a feedstock gas source (not shown) to the first gas separation membrane unit 11 through a feedstock gas supply line 26. The feedstock gas is pressurized by the compression part 21, so that the pressure thereof is increased.

After the feedstock gas is compressed by the compression part 21, the feedstock gas is cooled by the cooling part 23, and the condensate 53 containing moisture is separated and removed from the feedstock gas through the condensed flow line 24. The feedstock gas after the separation and removal of the condensate 53 is supplied into the first gas separation membrane unit 11 while being heated to a constant temperature by the heating part 25.

When the feedstock gas pressurized by the compression part 21 is supplied to the first gas separation membrane unit 11, the feedstock gas is separated into the first permeate gas, which is a gas that has permeated the gas separation membrane, and the first retentate gas, which is a gas that has not permeated the gas separation membrane, due to the difference between the gas permeation rates of the gas separation membrane.

The first retentate gas discharged from the first gas separation membrane unit 11 is a gas enriched in $CH_4$ as compared to the feedstock gas. The first retentate gas is discharged from the retentate gas outlet 11*b* of the first gas separation membrane unit 11, and is supplied to the second gas separation membrane unit 12 through the first line 14. On the other hand, the first permeate gas discharged from the first gas separation membrane unit 11 is enriched in $CO_2$ as compared to the feedstock gas. The first permeate gas is taken out of the system through the third line 18.

The first retentate gas discharged from the first gas separation membrane unit 11 is cooled by the cooling part 22, and the first retentate gas at a temperature lower than the operating temperature of the first gas separation membrane unit 11, T1, is supplied to the second gas separation membrane unit 12 to contact the gas separation membrane of the second gas separation membrane unit 12. Thus, the operating temperature of the second gas separation membrane unit 12, T2, is lower than the operating temperature of the first gas separation membrane unit 11. Under this temperature condition, the first retentate gas (second supply gas) is separated into the second permeate gas and the second retentate gas by the gas separation membrane of the second gas separation membrane unit 12. The second retentate gas discharged from the second gas separation membrane unit 12 is further enriched in $CH_4$. The second retentate gas may be supplied from the second retentate gas outlet 12*b* of the unit 12 to the liquefaction device 50 through the recovery line 15, to be further cooled and liquefied.

On the other hand, the second permeate gas is discharged from the second permeate gas outlet 12*c* of the second gas separation membrane unit 12, and is returned to the suction side of the compression part 21 in the feedstock gas supply line 26 via the second line 17 connected to the outlet 12*c*.

The second permeate gas discharged from the second gas separation membrane unit 12 and returned via the second line 17 is mixed with the feedstock gas and then pressurized by the compression part 21.

As described above, in the gas separation system of the present invention, the cooling part 22 lowers the operating temperature of the second gas separation membrane unit, T2, below the operating temperature of the first gas separation membrane unit 11, T1. In the second gas separation membrane unit 12, the separation selectivity between $CO_2$ and $CH_4$ in separation is improved due to the lower operating temperature. This enables a high $CH_4$ purity of the second retentate gas while reducing the amount of the second permeate gas that joins the feedstock gas supply line 26 through the second line 17 (hereinafter, the total amount of gases that join the feedstock gas from units other than the first gas separation membrane unit 11 is also referred to as an "amount of reflux"). Since the power for compression can be reduced by reducing the amount of reflux, high purity $CH_4$ can be produced at low cost according to the present invention. In the present embodiment, a hollow fiber membrane of polyimide, which has been conventionally used, is used as a gas separation membrane of the second gas separation membrane unit 12 at a controlled operating temperature, whereby the $CH_4$ purity can be effectively improved.

It is preferable to cool the second supply gas by the cooling part 22 such that the temperature of the first retentate gas (second supply gas) supplied to the second gas separation membrane unit is lower than the temperature of the feedstock gas (first supply gas) supplied to the first gas separation membrane unit 11, in view of lowering the operating temperature of the second gas separation membrane unit 12 with a simple system. Herein, the temperature of the gas supplied to a gas separation membrane unit refers to the temperature at the time when the gas is supplied to the gas inlet of the gas separation membrane unit.

In the present invention, the operating temperature of the first gas separation membrane unit 11, T1, is higher than the operating temperature of the second gas separation membrane unit 12, T2. As a result, a high throughput can be obtained even with a small membrane area due to a high $CO_2$ and $CH_4$ permeation rate of the first gas separation membrane unit 11, so that the equipment cost can be reduced.

Further, in the present embodiment, the second retentate gas whose temperature has already been lowered to a certain degree by the cooling part 22 can also be cooled by the liquefaction device 50. In this case, energy required for liquefaction in the liquefaction device can be reduced, so that liquefied methane can be produced at low cost.

In view of further increasing the $CH_4$ purity of the second retentate gas, the temperature of the second supply gas, t2, is preferably higher than the dew point for water of the second supply gas. By using the cooling part 23, the condensation flow line 24, and the heating part 25 described above, the dew point for the water of the second supply gas can be sufficiently lowered. The temperature of the second supply gas, 12, refers to the temperature of the first retentate gas at the time when the first retentate gas is supplied to the second gas separation membrane unit 12. On the other hand, the temperature of the first supply gas, t1, refers to the temperature of the feedstock gas at the time when the feedstock gas is supplied to the first gas separation membrane unit 11. When the temperature of the separation membrane is controlled by the temperature of the gas supplied to the unit, the operating temperatures of the first gas separation membrane unit 11 and the second gas separation membrane unit 12 can be regarded as the same temperature as the temperature of the first supply gas, t1, and the temperature of the second supply gas, t2, respectively.

The $CO_2$ permeation rate of the gas separation membrane of the second gas separation membrane unit at the operating temperature of the gas separation membrane of the second gas separation membrane unit, T2, is designated as $P_2'CO_2^{(T2)}$, and the $CO_2$ permeation rate of the first gas separation membrane unit at the operating temperature T1 is designated as $P_1'CO_2^{(T1)}$. The ratio of $P_2'CO_2^{(T2)}$ to $P_1'CO_2^{(T1)}$ is preferably 0.5 or more, more preferably 0.65 or more, and still more preferably 0.75 or more. In particular, $P_2'CO_2^{(T2)}$ is preferably larger than $P_1'CO_2^{(T2)}$ in view of reducing the membrane area. From such a point of view, the ratio of $P_2'CO_2^{(T2)}$ to $P_1'CO_2^{(T1)}$ is preferably more than 1, more preferably 1.4 or more, still more preferably 1.5 or more, and particularly preferably 1.7 or more. On the other hand, the ratio of $P_2'CO_2^{(T2)}$ to $P_1'CO_2^{(T1)}$ is preferably 7 or less, more preferably 6 or less, still more preferably 5 or less, and particularly preferably 4 or less.

In consideration of the above, the ratio of $P_2'CO_2^{(T2)}$ to $P_1'CO_2^{(T1)}$ is preferably 0.5 or more and 7 or less, more preferably 0.65 or more and 7 or less, still more preferably 0.75 or more and 7 or less, particularly preferably more than 1 and 7 or less, even more preferably 1.4 or more and 6 or less, yet more preferably 1.5 or more and 5 or less, and most preferably 1.7 or more and 4 or less.

Such $CO_2$ permeation rates can further enhance the effect of obtaining high purity $CH_4$ gas at low cost.

The separation selectivity of the gas separation membrane of the second gas separation membrane unit at the operating temperature of the second gas separation membrane unit, T2, is designated as $P_2'CO_2/P_2'CH_4^{(T2)}$, and the separation selectivity of the gas separation membrane of the first gas separation membrane unit at the operating temperature of the first gas separation membrane unit, T1, is designated as $P_1'CO_2/P_1'CH_4^{(T1)}$. The ratio of $P_2'CO_2/P_2'CH_4^{(T2)}$ to $P_1'CO_2/P_1'CH_4^{(T1)}$ is preferably 0.4 or more and 13 or less in view of effectively reducing the membrane area and also reducing the power for compression to obtain a high purity $CH_4$ gas at low cost, and the ratio is more preferably 0.5 or more and 12 or less, and still more preferably 0.6 or more and 7 or less. The ratio is particularly preferably 0.7 or more and 5 or less in view of further reducing the power for compression.

Such separation selectivities and $CO_2$ permeation rates can further enhance the effect of obtaining high purity $CH_4$ gas at low cost.

Preferably, the permeation rate of the gas separation membrane of the second gas separation membrane unit at 40° C., $P_2'CO_2^{(40)}$, is higher than the permeation rate of the gas separation membrane of the first gas separation membrane unit at 40° C., $P_1'CO_2^{(40)}$, in view of reducing the membrane area of the second gas separation membrane unit 12. From such a point of view, the ratio of the permeation rate of the gas separation membrane of the second gas separation membrane unit 12 at 40° C., $P_2'CO_2^{(40)}$, to the permeation rate of the gas separation membrane of the first gas separation membrane unit 11 at 40° C., $P_1'CO_2^{(40)}$, is preferably 1.1 or more, more preferably 1.2 or more, and still more preferably 1.4 or more. The ratio of $P_2'CO_2^{(40)}$ to $P_1'CO_2^{(40)}$ is preferably 12 or less, in view of availability of the gas separation membrane, and is preferably 5 or less in view of the purity of $CH_4$ gas.

Preferably, the separation selectivity of the gas separation membrane of the second gas separation membrane unit at 40° C., $P_2'CO_2/P_2'CH_4^{(40)}$, is lower than the separation selectivity of the gas separation membrane of the first gas separation membrane unit at 40° C., $P_1'CO_2'/P_1'CH_4^{(40)}$, in view of reducing the membrane area of the second gas separation membrane unit 12.

In view of further effectively reducing the membrane area of the second gas separation membrane unit 12, the ratio of the separation selectivity of the gas separation membrane of the second gas separation membrane unit 12 at 40° C., $P_2'CO_2/P_2'CH_4^{(40)}$, to the separation selectivity of the gas separation membrane of the first gas separation membrane unit 11 at 40° C., $P_1'CO_2/P_1'CH_4^{(40)}$, is preferably 0.8 or less, more preferably 0.75 or less, still more preferably 0.70 or less, and particularly preferably 0.60 or less. The ratio of $P_2'CO_2/P_2'CH_4^{(40)}$ to $P_1'CO_2/P_1'CH_4^{(40)}$ is preferably 0.2 or more in view of the availability of the gas separation membrane, and is preferably 0.3 or more in view of the purity of $CH_4$ gas.

A general operating temperature for membrane separation of $CO_2$ and $CH_4$ is 40° C., and therefore, the selectivity at this temperature is also defined as a measure in this embodiment.

The temperature of the first supply gas, t1, is preferably 0 to 60° C. more preferably 10 to 50° C., and still more preferably 20 to 40° C. When the temperature of the first supply gas, t1, is within the above-described range, $CH_4$ purity can be easily increased advantageously while reducing the membrane area by adjusting the $CO_2$ permeation rate. In addition, the gas separation membrane of the first gas separation membrane unit 11 of the present embodiment generally has higher $H_2O$ gas selectivity than $CH_4$ gas selectivity; accordingly, when the temperature of the first supply gas is within such a temperature range, condensation of water in the first gas separation membrane unit 11 can be prevented to allow for moisture permeation in the unit, so that the water content in the second supply gas can be reduced to lower the dew point.

A preferable range of the operating temperature of the first gas separation membrane unit 11, T1, may be the same as the preferable range of the temperature of the first supply gas, t1, and is preferably 0 to 60° C., more preferably 10 to 50° C., and still more preferably 20 to 40° C.

The temperature of the second supply gas, t2, is preferably 30° C. or less in view of much higher $CH_4$ purity of the second retentate gas and the larger effect of reducing the power needed for compression. From such a point of view, the temperature of the second supply gas is preferably 30° C. or lower, more preferably 25° C. or lower, still more preferably 20° C. or lower, and particularly preferably 10° C. or lower. The temperature of the second supply gas, t2, is preferably −50° C. or higher in view of avoiding poor gas separating performance of the second gas separation membrane unit 12 and in view of ease to obtain a temperature equal to or higher than the dew point for water of the first retentate gas supplied to the second gas separation membrane unit 12. The temperature 12 is more preferably −40° C. or higher, still more preferably −30° C. or higher, and particularly preferably −20° C. or higher.

A preferable range of the operating temperature of the second gas separation membrane unit 12, T2, may be the same as the preferable range of the temperature of the second supply gas, t2, and is preferably −50 to 30° C., more preferably −40 to 25° C., still more preferably −30 to 20° C., and particularly preferably −20° C. to 10° C.

The difference between the temperature of the first supply gas, t1, and the temperature of the second supply gas, 12, (i.e., t1−t2) is more preferably 10° C. or more in view of reducing the power for compression to enhance the effect of obtaining high purity $CH_4$ gas at low cost, and particularly preferably 15° C. or more. The temperature difference t1-t2 is preferably 110° C. or less, more preferably 90° C. or less, and particularly preferably 55° C. or less, in view of not too large a difference for preventing impairment of the function of the gas separation membrane and reducing the membrane area.

As with t1-t2, the temperature difference between the operating temperature of the first gas separation membrane unit 11, T1, and the operating temperature of the second gas separation membrane unit 12, T2, (i.e., T1-T2) is preferably 10° C. or more and 110° C. or less, more preferably 15° C. or more and 90° C. or less, and still more preferably 15° C. or more and 55° C. or less.

The difference between the temperature of the feedstock gas supplied to the system, T0, and the temperature of the feedstock gas at the time when it is sucked into the compression part 21, T0', (i.e., T0-T0') is preferably 2° C. or more in view of reducing the power for compression to enhance the effect of obtaining high purity $CH_4$ gas at low cost, and it is more preferably 3° C.' or more, still more preferably 7° C. or more, and particularly preferably 10° C. or more. The temperature difference T0-T0' is preferably 30° C. or less in view of not too large a difference for preventing freezing and blockage in the feedstock line.

For example, the dew point for water of the gas supplied to the second gas separation membrane unit 12 (hereinafter, also referred to as a "second supply gas") is preferably −70° C. or higher and 0° C. or lower, and more preferably −50° C. or higher and −8° C. or lower, but not limited thereto. The dew point is a temperature under the pressure of the second supply gas at the time of the gas being supplied to the second gas separation membrane unit 12.

Here, the dew point for water of the second supply gas tends to decrease as the amount of reflux decreases. The reason for this is as follows: the amount of water in the first supply gas is likely to be decreased by decreasing the amount of reflux, and accordingly, the dew point for water of the second supply gas decreases.

For this reason, the high purity CHA gas can be more easily obtained in the present invention.

In the present embodiment, the proportion of the amount of the gas flow refluxed from the gas separation membrane units other than the first gas separation membrane unit (F4) in the amount of the gas flow supplied to the first gas separation membrane unit (the amount of the flow of the first supply gas, F1) (hereinafter, also referred to as "reflux rate") is preferably 60% or less in view of further reducing the operation cost, and more preferably 50% or less. For example, the reflux rate is preferably 10% or more, in view of reducing the membrane area, and more preferably 20% or more.

In the present invention, the gas separation selectivity of the gas separation membrane of the first gas separation membrane unit at 40° C. ($CO_2$ permeation rate $P_1'CO_2$/$CH_4$ permeation rate $P_1'CH_4^{(40)}$) is preferably 30 or more and 150 or less, more preferably 35 or more and 130 or less, still more preferably 40 or more and 120 or less, and particularly preferably 50 or more and 110 or less, in view of efficiently obtaining high purity $CH_4$ with a high recovery rate.

In the present invention, the carbon dioxide permeation rate of the gas separation membrane of the first gas separation membrane unit at 40° C., $P_1'CO_2^{(40)}$, is preferably $1.5\times10^{-5}$ $cm^3$(STP)/$cm^2$·sec·cmHg or more and $100\times10^{-5}$ $cm^3$(STP)/$cm^2$·sec·cmHg or less, more preferably $2\times10^{-5}$ $cm^3$(STP)/$cm^2$·sec·cmHg or more and $45\times10^{-5}$ $cm^3$ (STP)/$cm^2$·sec·cmHg or less, still more preferably $3\times10^{-5}$ $cm^3$ (STP)/$cm^2$·sec·cmHg or more and $25\times10^{-5}$ $cm^3$(STP)/$cm^2$·sec·cmHg or less, and particularly preferably $7\times10^{-5}$ $cm^3$ (STP)/$cm^2$·sec·cmHg or more and $15\times10^{-5}$ $cm^3$ (STP)/$cm^2$·sec·cmHg or less, in view of obtaining high purity CHA with a high recovery rate while reducing the power for compression and the membrane area.

In the present invention, the $CH_4$ permeation rate of the gas separation membrane of the first gas separation membrane unit at 40° C., $P_1'CH_4^{(40)}$, is preferably $0.03\times10^{-5}$ $cm^3$(STP)/$cm^2$·sec·cmHg or more and $3\times10^{-5}$ $cm^3$(STP)/$cm^2$·sec·cmHg or less, more preferably $0.05\times10^{-5}$ $cm^3$ (STP)/$cm^2$·sec·cmHg or more and $0.8\times10^{-5}$ $cm^3$(STP)/$cm^2$·sec·cmHg or less, still more preferably $0.05\times10^{-5}$ $cm^3$ (STP)/$cm^2$·sec·cmHg or more and $0.5\times10^{-5}$ $cm^3$(STP)/$cm^2$·sec·cmHg or less, and particularly preferably $0.08\times10^{-5}$ $cm^3$(STP)/$cm^2$·sec·cmHg or more and $0.2\times10^{-5}$ $cm^3$(STP)/$cm^2$·sec·cmHg or less, in view of obtaining high purity $CH_4$ while reducing the power for compression and the membrane area.

Preferable ranges of the separation selectivity and the $CO_2$ permeation rate and $CH_4$ permeation rate of the first gas separation membrane unit 11 at the operating temperature of the first gas separation membrane unit, T1, may be the same as the preferable ranges of the separation selectivity and the $CO_2$ permeation rate and $CH_4$ permeation rate at 40° C.

In the present invention, the gas separation selectivity of the gas separation membrane of the second gas separation membrane unit at 40° C. (carbon dioxide permeation rate $P_2'CO_2$/$CH_4$ permeation rate $P_2'CH_4^{(40)}$ is preferably 5 or more and 150 or less, more preferably 10 or more and 90 or less, still more preferably 15 or more and 65 or less, and particularly preferably 20 or more and less than 55, in view of efficiently obtaining high purity $CH_4$ with a high recovery rate.

In the present invention, the carbon dioxide permeation rate of the gas separation membrane of the second gas separation membrane unit at 40° C., $P_2'CO_2^{(40)}$, is preferably $1.5\times10^{-5}$ $cm^3$(STP)/$cm^2$·sec·cmHg or more and $100\times10^{-5}$ $cm^3$ (STP)/$cm^2$·sec·cmHg or less, more preferably $7\times10^{-5}$ $cm^3$(STP)/$cm^2$·sec·cmHg or more and $90\times10^{-5}$ $cm^3$ (STP)/$cm^2$·sec·cmHg or less, particularly preferably $15\times10^{-5}$ $cm^3$ (STP)/$cm^2$·sec·cmHg or more and $80\times10^{-5}$ $cm^3$ (STP)/$cm^2$·sec·cmHg or less, and most preferably $20\times10^{-5}$ $cm^3$ (STP)/$cm^2$·sec·cmHg or more and $75\times10^{-5}$ $cm^3$ (STP)/$cm^2$·sec·cmHg or less, in view of obtaining high purity $CH_4$ with a high recovery rate while reducing the power for compression and the membrane area.

In the present invention, the $CH_4$ permeation rate of the gas separation membrane of the second gas separation membrane unit at 40° C., $P_2'CH_4^{(40)}$, is preferably $0.03\times10^{-5}$ $cm^3$ (STP)/$cm^2$·sec·cmHg or more and $3\times10^{-5}$ $cm^3$ (STP)/$cm^2$·sec·cmHg or less, more preferably $0.08/10^{-5}$ $cm^3$ (STP)/$cm^2$·sec·cmHg or more and $2.5\times10^{-5}$ $cm^3$(STP)/$cm^2$·sec·cmHg or less, still more preferably $0.3\times10^{-5}$ $cm^3$ (STP)/$cm^2$·sec·cmHg or more and $1.5\times10^{-5}$ $cm^3$ (STP)/$cm^2$·sec·cmHg or less, and particularly preferably $0.8\times10^{-5}$ $cm^3$ (STP)/$cm^2$·sec·cmHg or more and $1.5\times10^{-5}$ $cm^3$ (STP)/$cm^2$·sec·cmHg or less, in view of obtaining high purity $CH_4$ while reducing the power for compression and the membrane area.

It is preferable to cool the second supply gas such that the separation selectivity of the gas separation membrane of the second gas separation membrane unit at the operating temperature of the second gas separation membrane unit 12, T2, (i.e., $P_2'CO_2/P_2'CH_4^{(T2)}$) is 15 or more and 3000 or less, in view of effectively reducing the membrane area and also reducing the power for compression to obtain high purity $CH_4$ gas at low cost, and it is more preferable to cool the second supply gas such that the separation selectivity is 20 or more and 1400 or less, even more preferably 30 or more and 800 or less, and particularly preferably 30 or more and 700 or less. The separation selectivity at the temperature of the second supply gas, T2, is also preferably in the same numerical range as of the separation selectivity of the gas separation membrane of the second gas separation membrane unit, $P_2'CO_2/P_2'CH_4^{(T2)}$.

It is preferable to cool the second supply gas such that the $CO_2$ permeation rate of the gas separation membrane of the second gas separation membrane unit at the operating temperature of the second gas separation membrane unit 12, T2, (i.e., $P_2'CO_2^{(T2)}$ is $3\times10^{-5}$ $cm^3$ (STP)/$cm^2$·sec·cmHg or more and $80\times10^{-5}$ $cm^3$(STP)/$cm^2$·sec·cmHg or less, in view of effectively reducing the membrane area and also reducing the power for compression to obtain high purity $CH_4$ gas at low cost, and it is more preferable to cool the second supply gas such that the $CO_2$ permeation rate is $4\times10^{-5}$ $cm^3$(STP)/$cm^2$·sec·cmHg or more and $60\times10^{-5}$ $cm^3$(STP)/$cm^2$·sec·cmHg or less, even more preferably $5\times10^{-5}$ $cm^3$ (STP)/$cm^2$·sec·cmHg or more and $55\times10^{-5}$ $cm^3$(STP)/$cm^2$·sec·cmHg or less, and particularly preferably $6\times10^{-5}$ $cm^3$(STP)/$cm^2$·sec·cmHg or more and $50\times10^{-5}$ $cm^3$(STP)/$cm^2$·sec·cmHg or less. The $CO_2$ permeation rate at the temperature of the second supply gas, t2, is also preferably in the same numerical range as of the $CO_2$ permeation rate of the gas separation membrane of the second gas separation membrane unit, $P_2'CO_2^{(T2)}$.

It is preferable to cool the second supply gas such that the $CH_4$ permeation rate of the gas separation membrane of the second gas separation membrane unit at the operating temperature of the second gas separation membrane unit 12, T2, (i.e., $P_2'CH_4$) is $0.002\times10^{-5}$ $cm^3$ (STP)/$cm^2$·sec·cmHg or more and $1\times10^{-5}$ $cm^3$ (STP)/$cm^2$·sec·cmHg or less in view of effectively reducing the membrane area and also reducing the power for compression to obtain high purity $CH_4$ gas at low cost, and it is more preferable to cool the second supply gas such that the $CH_4$ permeation rate is $0.005\times10^{-5}$ $cm^3$ (STP)/$cm^2$·sec·cmHg or more and $0.8\times10^{-5}$ $cm^3$ (STP)/$cm^2$·sec·cmHg or less, even more preferably $0.01\times10^{-5}$ $cm^3$ (STP)/$cm^2$·sec·cmHg or more and $0.6\times10^{-5}$ $cm^3$ (STP)/$cm^2$·sec·cmHg or less, and particularly preferably $0.01\times10^{-5}$ $cm^3$ (STP)/$cm^2$·sec·cmHg or more and $0.5\times10^{-5}$ $cm^3$ (STP)/$cm^2$·sec·cmHg or less. The $CH_4$ permeation rate at the temperature of the second supply gas, t2, is also preferably in the same numerical range as of the $CH_4$ permeation rate of the gas separation membrane of the second gas separation membrane unit $P_2'CH_4^{(T2)}$.

In the present invention, the $CO_2$ concentration of the second retentate gas obtained is preferably 100 ppm or less, more preferably 50 ppm or less, on a volume basis. This is because such high-purity CHA gas with few impurities is capable of being liquefied.

The $H_2O$ concentration of the second retentate gas obtained is preferably 50 ppm or less, more preferably 20 ppm or less, on a volume basis. This is because such high-purity $CH_4$ gas with few impurities is capable of being liquefied.

The feedstock gas used in the present invention is a gas containing at least $CO_2$ and $CH_4$, and examples thereof include biogas, landfill gas, and natural gas. The biogas is a gas generated when a biomass feedstock is brought into contact with a microorganism under anaerobic conditions to perform a fermentation treatment such as $CH_4$ fermentation by the microorganism. Examples of the biomass feedstock include organic matters such as food waste, agricultural residue, sewage sludge, and livestock waste. The landfill gas refers to a gas generated by microbial decomposition or the like of organic matter in a waste landfill. Biogas and landfill gas are typically composed mainly of $CO_2$ and $CH_4$.

In the present invention, the feedstock gas preferably contains $CH_4$ in an amount of 30 mol % or more, particularly preferably 40 to 95 mol %. In the present invention, the feedstock gas preferably contains 3 to 70 mol % of $CO_2$ in view of greater technical contribution of the present invention, and particularly preferably contains 5 to 60 mol % of $CO_2$.

The $CO_2$ concentration of the first permeate gas is preferably 85 to 99 mol %, and more preferably 88 to 98 mol %.

The $CO_2$ concentration of the first retentate gas is preferably 5 to 45 mol %, and more preferably 8 to 40 mol %.

The $CO_2$ concentration of the second permeate gas is preferably 20 to 85 mol %, and more preferably 25 to 80 mol %.

The pressure of the compression part 21 is generally preferably 0.2 MPaG or more and 3.0 MPaG or less, and more preferably 0.3 MPaG or more and 2.4 MPaG or less, in terms of the pressure of the gas supplied to the first gas separation membrane unit 11.

Next, a gas separation system 10' according to the second embodiment of the present invention will be described with reference to FIG. 3. In the description of the second embodiment, the same components as those of the first embodiment are denoted by the same reference numerals, and description thereof is omitted. Differences from the first embodiment will be mainly described.

In a gas separation system 10' shown in FIG. 3, a first gas separation membrane unit 11 and a third gas separation membrane unit 13 are connected in series. Specifically, the first gas separation membrane unit 11 and the third gas separation membrane unit 13 are connected by connecting the permeate gas outlet 11*c* of the first gas separation membrane unit 11 and the gas inlet 13*a* of the third gas separation membrane unit 13 by the third line 18. As the gas separation membrane module of the third gas separation membrane unit 13, the same modules as those described for the first gas separation membrane unit 11 and the second gas separation membrane unit 12 can be employed.

In the third gas separation membrane unit 13, the retentate gas outlet 13*b* is connected to the feedstock gas supply line 26 by a fourth line 41. In the embodiment of FIG. 3, the fourth line 41 is connected to the feedstock gas supply line 26 at a position on the suction side of the compression part 21. In the example of FIG. 3, the third permeate gas discharge line 19 is connected to the permeate gas outlet 13*c* of the third gas separation membrane unit 13.

The compression part 21 is disposed for the purpose of pressurizing the third retentate gas returned from the third gas separation membrane unit 13 in addition to the feedstock gas supplied from the gas source and the second permeate gas returned from the second gas separation membrane unit 12.

The path for gas during operation for gas separation in the gas separation system 10' of the present embodiment having the above configuration will be described with reference to FIG. 3. The feedstock gas to be separated is supplied from the mixed gas source (not shown) to the first gas separation membrane unit 11 through the feedstock gas supply line 26. Prior to the supply, the feedstock gas is pressurized by the compression part 21, and the pressure thereof is thus increased.

As in the first embodiment, the feedstock gas pressurized by the compression part 21 is supplied to the first gas separation membrane unit 11, and the feedstock gas is separated into the first permeate gas and the first retentate gas. The first permeate gas discharged from the first gas separation membrane unit 11 is supplied to the third gas separation membrane unit 13 through the third line 18. The first permeate gas introduced into the third gas separation membrane unit 13 is separated into the third permeate gas and the third retentate gas by the unit 13. The third permeate gas is further rich in $CO_2$ as compared to the first permeate gas introduced into the third gas separation membrane unit 13, and is taken out of the system from the permeate gas outlet 13*c* of the unit 13 through the third permeate gas discharge line 19. On the other hand, the third retentate gas is discharged from the retentate gas outlet 13*b* of the third gas separation membrane unit 13, and is returned to the suction side of the compression part 21 in the feedstock gas supply line 26 via the fourth line 41 connected to the outlet 13*b*. The third retentate gas returned through the line 41 is mixed with the feedstock gas and then pressurized by the compression part 21.

In the third line 18, the second compression part may or may not be disposed.

In the gas separation system 10' of the present embodiment, the operating temperature of the second gas separation membrane unit, T2, is preferably lowered by the cooling part 22, below the operating temperature of the third gas separation membrane unit 13, T3. As a result, the $CO_2$ permeation rate and $CH_4$ permeation rate of the third gas separation membrane unit 13 can be increased, so that the membrane area of the third gas separation membrane unit 13 can be reduced to reduce the equipment cost.

In view of simplifying the system, the second supply gas is preferably cooled by the cooling part 22 such that the temperature of the second supply gas supplied to the second gas separation membrane unit, t2, is lower than the temperature of the first permeate gas supplied to the third gas separation membrane unit 13 (third supply gas), t3, to lower the operating temperature of the second gas separation membrane unit, T2, below the operating temperature of the third gas separation membrane unit 13, T3.

The $CO_2$ permeation rate of the gas separation membrane of the second gas separation membrane unit at the operating temperature of the second gas separation membrane unit, T2, is designated as $P_2'CO_2^{(T2)}$, and the $CO_2$ permeation rate of the gas separation membrane of the third gas separation membrane unit at the operating temperature T3 is designated as $P_3'CO_2^{(T3)}$. The ratio of $P_2'CO_2^{(T2)}$ to $P_3'CO_2^{(T3)}$ is preferably 0.5 or more, more preferably 0.65 or more, and still more preferably 0.75 or more. $P_2'CO_2^{(T2)}$ is preferably larger than $P_3'CO_2^{(T3)}$ in view of reducing the membrane area. From such a point of view, the ratio of $P_2'CO_2^{(T2)}$ to $P_3'CO_2^{(T3)}$ is preferably more than 1, more preferably 1.4 or more, still more preferably 1.5 or more, and particularly preferably 1.7 or more. On the other hand, the ratio of $P_2'CO_2^{(T2)}$ to $P_3'CO_2^{(T3)}$ is preferably 7 or less, more preferably 6 or less, still more preferably 5 or less, and particularly preferably 4 or less.

Such $CO_2$ permeation rates can further enhance the effect of obtaining high purity $CH_4$ gas at low cost.

At the temperature of the second supply gas, the separation selectivity of the gas separation membrane of the second gas separation membrane unit at the operating temperature of the second gas separation membrane unit, T2, is designated as $P_2'CO_2/P_2'CH_4^{(T2)}$, and the separation selectivity of the gas separation membrane of the third gas separation membrane unit at the operating temperature of the third gas separation membrane unit, T3, is designated as $P_3'CO_2/P_3'CH_4^{(T3)}$. The ratio of $P_2'CO_2/P_2'CH_4^{(T2)}$ to $P_3'CO_2/P_3'CH_4^{(T3)}$ is preferably 0.4 or more and 13 or less in view of effectively reducing the membrane area to obtain a high purity $CH_4$ gas at low cost, and the ratio is more preferably 0.5 or more and 12 or less. Also in view of reducing the power for compression, it is more preferably 0.6 or more and 7 or less, and particularly preferably 0.7 or more and 5 or less.

The permeation rate of the gas separation membrane of the second gas separation membrane unit at 40° C., $P_2'CO_2^{(40)}$, is preferably higher than the permeation rate of the gas separation membrane of the third gas separation membrane unit at 40° C., $P_3'CO_2^{(40)}$, in view of reducing the membrane area of the second gas separation membrane unit 12. From such a point of view, the ratio of the permeation rate of the gas separation membrane of the second gas separation membrane unit 12 at 40° C., $P_2'CO_2^{(40)}$, to the permeation rate of the gas separation membrane of the third gas separation membrane unit 13 at 40° C., $P_3'CO_2^{(40)}$, is preferably 1.1 or more, more preferably 1.2 or more, and still more preferably 1.4 or more. The ratio of $P_2'CO_2^{(40)}$ to $P_3'CO_2^{(40)}$ is preferably 12 or less, in view of availability of the gas separation membrane, and is preferably 5 or less in view of the purity of $CH_4$ gas.

The separation selectivity of the gas separation membrane of the second gas separation membrane unit at 40° C., $P_2'CO_2/P_2'CH_4^{(40)}$, is preferably lower than the separation selectivity of the gas separation membrane of the third gas separation membrane unit at 40° C., $P_3'CO_2/P_3'CH_4^{(40)}$, in view of further reducing the membrane area of the second gas separation membrane unit 12.

A general operating temperature for membrane separation of $CO_2$ and $CH_4$ is 40° C., and therefore, the selectivity at this temperature is defined as a measure in this embodiment.

In view of further effectively reducing the membrane area of the second gas separation membrane unit 12, the ratio of the separation selectivity of the gas separation membrane of the second gas separation membrane unit 12 at 40° C., $P_2'CO_2/P_2'CH_4^{(40)}$, to the separation selectivity of the gas separation membrane of the third gas separation membrane unit 13 at 40° C., $P_3'CO_2/P_3'CH_4^{(40)}$, is preferably 0.8 or less, more preferably 0.75 or less, still more preferably 0.70 or less, and particularly preferably 0.60 or less. The ratio of $P_2'CO_2/P_2'CH_4^{(40)}$ to $P_3'CO_2/P_3'CH_4^{(40)}$ is preferably 0.2 or more in view of availability of the gas separation membrane, and is preferably 0.3 or more in view of the purity of $CH_4$ gas.

The temperature of the third supply gas, t3, is preferably 0 to 60° C., more preferably 10 to 50° C., and still more preferably 20 to 40° C. When the temperature of the third supply gas, t3, is within the above-described range, $CH_4$ purity can be easily increased advantageously while reducing the membrane area by adjusting the $CO_2$ permeation rate.

A preferable temperature range of the operating temperature of the third gas separation membrane unit 13 may be the same as the preferable range of the temperature of the third supply gas, t3.

The difference between the temperature of the third supply gas, t3, and the temperature of the second supply gas, t2, (i.e., t3-t2) is preferably 10° C. or more, in view of reducing the power for compression to enhance the effect of obtaining high purity $CH_4$ gas at low cost, and more preferably 15° C. or more. The temperature difference t3-t2 is preferably 110° C. or less, more preferably 90° C. or less, and particularly preferably 55° C. or less, in view of not too large a difference for preventing impairment of the function of the gas separation membrane and reducing the membrane area.

As with t3-t2, the temperature difference between the operating temperature of the third gas separation membrane unit 13, T3, and the operating temperature of the second gas separation membrane unit 12, T2, (i.e., T3-T2) is preferably 10° C. or more and 110° C. or less, more preferably 15° C. or more and 90° C. or less, and still more preferably 15° C. or more and 55° C. or less.

In the present embodiment, the proportion of the amount of the gas flow refluxed from the gas separation membrane units other than the first gas separation membrane unit (F4) in the amount of the gas flow supplied to the first gas separation membrane unit (the amount of the flow of the first supply gas, F1) (hereinafter, also referred to as "reflux rate") is preferably 70% or less in view of further reducing the operation cost, and more preferably 60% or less. The reflux rate is, for example, preferably 10% or more in view of reducing the membrane area, and preferably 20% or more. In the present embodiment, F4 is the total amount of the second permeate gas of the second gas separation membrane unit 12 and the third retentate gas of the third gas separation membrane unit 13.

In the present invention, the gas separation selectivity of the gas separation membrane of the third gas separation membrane unit at 40° C. ($P_3'CO_2/CH_4$ permeation rate $P_3'CH_4^{(40)}$ is preferably 30 or more and 150 or less, more preferably 35 or more and 130 or less, still more preferably 40 or more and 120 or less, and particularly preferably 50 or more and 110 or less, in view of efficiently obtain high purity $CH_4$ with a high recovery rate.

In the present invention, the carbon dioxide permeation rate of the gas separation membrane of the third gas separation membrane unit at 40° C., $P_3'CO_2^{(40)}$, is preferably $1.5\times10^{6}$ $cm^3(STP)/cm^2\cdot sec\cdot cmHg$ or more and $100\times10^{-5}$ $cm^3(STP)/cm^2\cdot sec\cdot cmHg$ or less, more preferably $2\times10^{-5}$ $cm^3(STP)/cm^2\cdot sec\cdot cmHg$ or more and $45\times10^{-5}$ $cm^3(STP)/cm^2\cdot sec\cdot cmHg$ or less, still more preferably $3\times10^{-5}$ $cm^3(STP)/cm^2\cdot sec\cdot cmHg$ or more and $25\times10^{-5}$ $cm^3(STP)/cm^2\cdot sec\cdot cmHg$ or less, and particularly preferably $7\times10^{-5}$ $cm^3(STP)/cm^2\cdot sec\cdot cmHg$ or more and $15\times10^{-5}$ $cm^3(STP)/cm^2\cdot sec\cdot cmHg$ or less, in view of obtaining high purity $CH_4$ with a high recovery rate while reducing the power for compression and the membrane area.

In the present invention, the $CH_4$ permeation rate of the gas separation membrane of the third gas separation membrane unit at 40° C., $P_3'CH_4^{(40)}$, is preferably $0.03\times10^{-5}$ $cm^3$(STP)/$cm^2$·sec·cmHg or more and $3\times10^{-5}$ $cm^3$(STP)/$cm^2$·sec·cmHg or less, more preferably $0.05\times10^{-5}$ $cm^3$(STP)/$cm^2$·sec·cmHg or more and $0.8\times10^{-5}$ $cm^3$(STP)/$cm^2$·sec still more preferably $0.05\times10^{-5}$ $cm^3$(STP)/$cm^2$·sec·cmHg or more and $0.5\times10^{-5}$ $cm^3$(STP)/$cm^2$·sec·cmHg or less, and particularly preferably $0.08\times10^{-6}$ $cm^3$(STP)/$cm^2$·sec·cmHg or more and $0.2\times10^{-5}$ $cm^3$(STP)/$cm^2$·sec·cmHg or less, in view of obtaining high purity $CH_4$ while reducing the power for compression and the membrane area.

The $CO_2$ concentration of the first permeate gas is preferably 80 to 99 mol %, and more preferably 83 to 95 mol %.

The $CO_2$ concentration of the first retentate gas is preferably 5 to 30 mol %, and more preferably 10 to 25 mol %.

The $CO_2$ concentration of the second permeate gas is preferably 25 to 65 mol %, and more preferably 30 to 60 mol %.

The $CO_2$ concentration of the third permeate gas is preferably 95 to 99.8 mol %, and more preferably 98 to 99.5 mol %.

The $CO_2$ concentration of the third retentate gas is preferably 55 to 90 mol %, and more preferably 60 to 85 mol %.

Preferable ranges of the separation selectivity and the $CO_2$ permeation rate and $CH_4$ permeation rate of the third gas separation membrane unit 13 at the operating temperature of the third gas separation membrane unit, T3, may be the same as the preferable ranges of the separation selectivity and the $CO_2$ permeation rate and $CH_4$ permeation rate at 40° C.

The pressure of the compression part 21 is generally preferably 0.05 MPaG or more and 1.2 MPaG or less, and more preferably 0.1 MPaG or more and 1.0 MPaG or less, in terms of the pressure of the gas supplied to the third gas separation membrane unit 13.

Although the present invention has been described based on the preferred embodiments thereof, the present invention is not limited to these embodiments. For example, though a unit including a gas separation membrane module having a hollow fiber membrane is used as an example of each gas separation membrane unit in the above embodiments, another type of gas separation membrane module may be used instead.

Further, in addition to the compression part in the above-described embodiment, a decompression part may be provided on the permeate side of any one or two of the gas separation membrane units to apply power to the mixed gas supplied to the gas separation membrane unit to pass through the separation membrane. As such a decompression part, a known vacuum pump can be used, for example.

For example, when a biogas is used as the feedstock gas, the feedstock gas may be subjected to a pretreatment for removing impurities such as siloxane, volatile organic compounds, and organic compounds having two or more carbon atoms, and then the feedstock gas after the removal may be supplied to the system 10.

The cooled second retentate gas may be used to lower the operating temperature of the second gas separation membrane unit 12.

Figure 4:
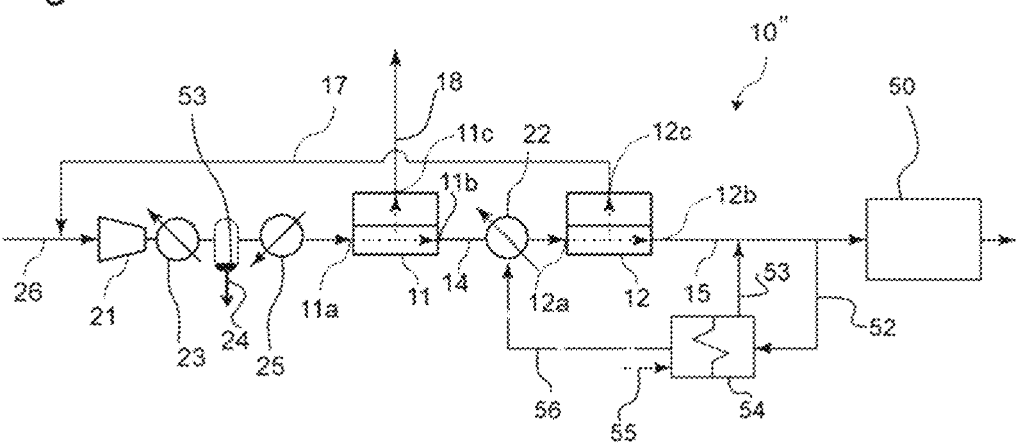
FIG. 4 is a schematic diagram showing a configuration of a gas separation system according to still another embodiment of the present invention.

For example, as shown in FIG. 4, the cooled second retentate gas is introduced into the heat exchanger 54 through a line 52 branched from the recovery line 15 to cool the liquid medium 55 separately introduced into the heat exchanger 54. The cooled liquid medium 55 is used for cooling in the cooling part 22 through the line 56. The second retentate gas used for cooling the liquid medium 55 is returned to the recovery line 15 through the line 53. Alternatively, as shown in FIG. 5, the second retentate gas liquefied by the liquefaction device 50 may be introduced as the cooled second retentate gas into the heat exchange device 54 serving as the methane vaporization device through the line 59, and the liquid medium 55 may be cooled by the heat of vaporization of the liquefied second retentate gas.

Figure 6:
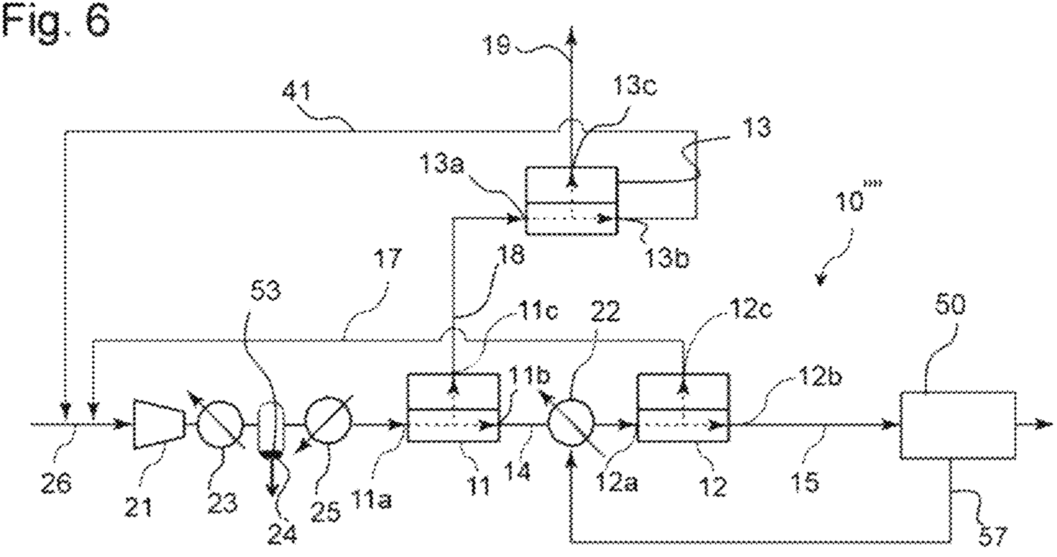
FIG. 6 is a schematic diagram showing a configuration of a gas separation system according to still another embodiment of the present invention.

Alternatively, as shown in FIG. 6, the second retentate gas liquefied by the liquefaction device 50 may be supplied to the cooling part 22 through a line 57 to be used as a cooling refrigerant of the cooling part 22, and the first retentate gas may be cooled by exchanging heat therewith.

Figure 5:
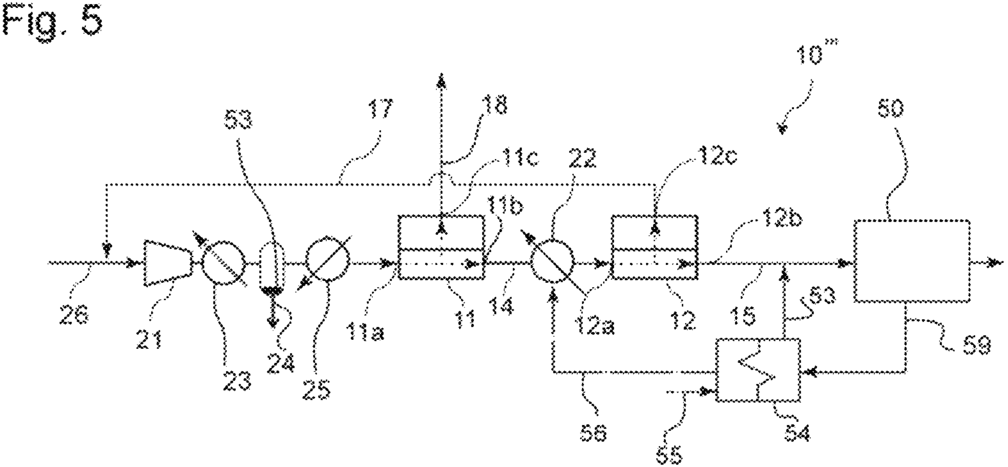
FIG. 5 is a schematic diagram showing a configuration of a gas separation system according to still another embodiment of the present invention.

In the embodiments of FIGS. 4 to 6, the other points are the same as those of the embodiments of FIGS. 1 and 3.

EXAMPLES

Hereinafter, the present invention will be described in more detail by way of Examples. However, the scope of the present invention is not limited by these examples. In each of Examples and Comparative Examples, the $H_2O$ concentration of the obtained gas product (second retentate gas) was 2 ppm or less on a volume basis. In each of Examples and Comparative Examples, the temperature of the first supply gas was 40° C.

<Gas Separation Membrane Module>

The gas separation characteristics at 40° C. of the gas separation membrane modules used in Examples and Comparative Examples are shown in Table 1. In the gas separation membrane modules, aromatic polyimide hollow fiber membranes as a gas separation membrane were packed in a housing. The gas separation membrane module A includes a gas separation membrane having higher gas separation selectivity and lower gas permeation rate than those of the gas separation membrane module B. The unit for P'$CO_2$ and P'$CH_4$ in Table 1 is $\times10^{-5}$ $cm^3$(STP)/$cm^2$·sec·cmHg.

TABLE 1

| Separation membrane module | Temperature ° C. | P'CO2 | P'CH4 | P'CO2/P'CH4 | Membrane area per module m2 |
|---|---|---|---|---|---|
| A | 40 | 9.9 | 0.18 | 55 | 24 |
| | 25 | 9.0 | 0.12 | 78 | |
| | 10 | 8.0 | 0.07 | 114 | |
| | −5 | 7.1 | 0.041 | 173 | |
| | −20 | 6.2 | 0.022 | 277 | |
| B | 40 | 21 | 0.82 | 26 | 20 |
| | 25 | 20 | 0.6 | 33 | |
| | 10 | 18 | 0.42 | 43 | |
| | −5 | 17 | 0.28 | 61 | |
| | −20 | 15 | 0.18 | 83 | |

Unit of gas permeation rate is ×10 · 5 cm3 (STP)/cm2 · sec · cmHg

Comparative Example 1

Separation of a mixed gas containing carbon dioxide and $CH_4$ was performed using the gas separation system 10 shown in FIG. 1 to obtain $CH_4$ as a product gas.

The feedstock gas used was a composition containing 39.8 mol % of $CO_2$, 59.7 mol % of $CH_4$, and 0.5 mol % of $H_2O$, and the flow rate of the gas flowing into the system was 200 Nm3/h.

The cooling part 22 was not operated. The gas separation membrane module A was used for each of the first gas separation membrane unit 11 and the second gas separation membrane unit 12. A compressor was used as the compression part 21 in the system 10.

Examples 1-1 to 1-4

A product gas was obtained in the same manner as in Comparative Example 1, except that the cooling unit 22 was operated to change the temperature of the second supply gas by the degree of temperature drop (first retentate gas→second supply gas) shown in Table 2 to thereby lower the operating temperature of the second gas separation membrane unit 12 below the operating temperature of the first gas separation membrane unit 11. The degree of temperature drop in Table 2 is a value obtained by subtracting the temperature of the second supply gas supplied to the second gas separation membrane unit 12 unit from the temperature of the retentate gas discharged from the first gas separation membrane unit 11.

Comparative Example 2

A product gas was obtained in the same manner as in Comparative Example 1 except that the gas separation membrane module B was used for the second gas separation membrane unit 12.

Examples 2-1 to 2-4

A product gas was obtained in the same manner as in Comparative Example 2, except that the cooling unit 22 was operated to change the temperature of the second supply gas by the degree of temperature drop (first retentate gas→second supply gas) shown in Table 2 to thereby lower the operating temperature of the second gas separation membrane unit 12 below the operating temperature of the first gas separation membrane unit 11.

Comparative Example 3

This example was carried out in the same manner as in Comparative Example 1 except that the gas separation system 10' shown in FIG. 3 was used. The gas separation membrane module A was used for the third gas separation membrane unit 13. A compressor was used as the compression part 21 in the system 10. The feedstock gas used was a composition containing 39.8 mol % of $CO_2$. 59.7 mol % of $CH_4$, and 0.5 mol % of $H_2O$. The flow rate of the feedstock gas flowing into the system was 200 Nm3/h.

Examples 3-1 to 3-4

A product gas was obtained in the same manner as in Comparative Example 3, except that the cooling unit 22 was operated to change the temperature of the second supply gas by the degree of temperature drop (first retentate gas→second supply gas) shown in Table 3 to thereby lower the operating temperature of the second gas separation membrane unit 12 below the operating temperature of the first gas separation membrane unit 11 and the operating temperature of the third gas separation membrane unit 13.

Comparative Example 4

A product gas was obtained in the same manner as in Comparative Example 3 except that the gas separation membrane module B was used for the second gas separation membrane unit 12.

Examples 4-1 to 4-4

A product gas was obtained in the same manner as in Comparative Example 4, except that the cooling unit 22 was operated to change the temperature of the second supply gas by the degree of temperature drop (first retentate gas→second supply gas) shown in Table 3 to thereby lower the operating temperature of the second gas separation membrane unit 12 below the operating temperature of the first gas separation membrane unit 11 and the operating temperature of the third gas separation membrane unit 13.

TABLE 2

| | | | Comp. Ex. 1 | Ex. 1-1 | Ex. 1-2 | Ex. 1-3 | Ex. 1-4 | Comp. Ex. 2 | Ex. 2-1 | Ex. 2-2 | Ex. 2-3 | Ex. 2-4 |
|---|---|---|---|---|---|---|---|---|---|---|---|---|
| Feedstock gas | Temperature (T0) | ° C. | 40 | 40 | 40 | 40 | 40 | 40 | 40 | 40 | 40 | 40 |
| Gas sucked | Temperature (T0') | ° C. | 40 | 36 | 33 | 30 | 27 | 40 | 35 | 30 | 27 | 24 |
| Operating pressure | First gas separation membrane unit | MPaG | 1.0 | 1.0 | 1.0 | 1.0 | 1.0 | 1.0 | 1.0 | 1.0 | 1.0 | 1.0 |
| Compressor | Power for compression | kW | 31 | 29 | 28 | 27 | 26 | 37 | 34 | 31 | 29 | 28 |
| Operating temperature (° C.) | First gas separation membrane unit (T1) | ° C. | 40 | 40 | 40 | 40 | 40 | 40 | 40 | 40 | 40 | 40 |
| | Second gas separation membrane unit (T2) | ° C. | 40 | 25 | 10 | −5 | −20 | 40 | 25 | 10 | −5 | −20 |
| Degree of temperature drop | First retentate gas ↓ Second supply gas | Δ° C. | 0 | 15 | 30 | 45 | 60 | 0 | 15 | 30 | 45 | 60 |
| | Feedstock gas ⇒ Gas sucked | | 0 | 4 | 7 | 10 | 13 | 0 | 5 | 10 | 13 | 16 |
| Dew point (under pressure) | Second supply gas | ° C. | −33 | −35 | −38 | −40 | −42 | −22 | −26 | −30 | −33 | −36 |
| Gas separation selectivity 1) | First gas separation membrane unit | — | 1.00 | 1.00 | 1.00 | 1.00 | 1.00 | 1.00 | 1.00 | 1.00 | 1.00 | 1.00 |
| | Second gas separation membrane unit | | 1.00 | 1.00 | 1.00 | 1.00 | 1.00 | 0.46 | 0.46 | 0.46 | 0.46 | 0.46 |

TABLE 2-continued

| | | | Comp. Ex. 1 | Ex. 1-1 | Ex. 1-2 | Ex. 1-3 | Ex. 1-4 | Comp. Ex. 2 | Ex. 2-1 | Ex. 2-2 | Ex. 2-3 | Ex. 2-4 |
|---|---|---|---|---|---|---|---|---|---|---|---|---|
| Amount of gas flow | First supply gas (F1) | $Nm^3/h$ | 279 | 268 | 259 | 252 | 247 | 331 | 309 | 291 | 277 | 266 |
| | Second supply gas (F2) | | 193 | 182 | 173 | 166 | 161 | 246 | 223 | 205 | 191 | 180 |
| Amount of gas flow refluxed | Second permeate + Third retentate (F4) | | 79 | 68 | 59 | 52 | 47 | 131 | 109 | 91 | 77 | 66 |
| Reflux rate | (F4)/(F1) | % | 28 | 25 | 23 | 21 | 19 | 40 | 35 | 31 | 28 | 25 |
| CO2 concentration | First supply gas | mol % | 41 | 41 | 42 | 42 | 43 | 39 | 39 | 40 | 41 | 41 |
| | First permeate gas | | 93 | 93 | 93 | 93 | 93 | 93 | 93 | 93 | 93 | 93 |
| | First retentate gas | | 18 | 17 | 17 | 16 | 16 | 20 | 19 | 18 | 17 | 17 |
| | Second permeate gas | | 43 | 46 | 49 | 52 | 55 | 37 | 39 | 41 | 43 | 46 |
| Number of modules | First gas separation membrane unit | pc | 6 | 6 | 6 | 6 | 6 | 6 | 6 | 6 | 6 | 6 |
| | Second gas separation membrane unit | | 43 | 54 | 72 | 102 | 160 | 21 | 23 | 26 | 31 | 39 |
| | Total | | 49 | 60 | 78 | 108 | 166 | 27 | 29 | 32 | 37 | 45 |
| Product gas | CO2 concentration | | ≤50 ppmv | ≤50 ppmv | ≤50 ppmv | ≤50 ppmv | ≤50 ppmv | ≤50 ppmv | ≤50 ppmv | ≤50 ppmv | ≤50 ppmv | ≤50 ppmv |
| | CH4 recovery rate | % | 95.7 | 95.7 | 95.7 | 95.6 | 95.6 | 95.7 | 95.7 | 95.7 | 95.7 | 95.7 |

1) Relative value to gas separation selectivity of first gas separation membrane unit (at 40° C.)

TABLE 3

| | | | Comp. Ex. 3 | Ex. 3-1 | Ex. 3-2 | Ex. 3-3 | Ex. 3-4 | Comp. Ex. 4 | Ex. 4-1 | Ex. 4-2 | Ex. 4-3 | Ex. 4-4 |
|---|---|---|---|---|---|---|---|---|---|---|---|---|
| Feedstock gas | Temperature (T0) | ° C. | 40 | 40 | 40 | 40 | 40 | 40 | 40 | 40 | 40 | 40 |
| Gas sucked | Temperature (T0') | ° C. | 40 | 37 | 34 | 32 | 30 | 40 | 35 | 32 | 29 | 27 |
| Operating pressure | First gas separation membrane unit | MPaG | 1.0 | 1.0 | 1.0 | 1.0 | 1.0 | 1.0 | 1.0 | 1.0 | 1.0 | 1.0 |
| | Third gas separation membrane unit | | 0.18 | 0.18 | 0.18 | 0.18 | 0.18 | 0.18 | 0.18 | 0.18 | 0.18 | 0.18 |
| Compressor | Power for compression | kW | 38 | 36 | 35 | 34 | 33 | 43 | 40 | 38 | 36 | 34 |
| Operating temperature (° C.) | First gas separation membrane unit (T1) | ° C. | 40 | 40 | 40 | 40 | 40 | 40 | 40 | 40 | 40 | 40 |
| | Second gas separation membrane unit (T2) | ° C. | 40 | 25 | 10 | −5 | −20 | 40 | 25 | 10 | −5 | −20 |
| | Third gas separation membrane unit (T3) | ° C. | 40 | 40 | 40 | 40 | 40 | 40 | 40 | 40 | 40 | 40 |
| Degree of temperature drop | First retentate gas ⬇ Second supply gas | Δ° C. | 0 | 15 | 30 | 45 | 60 | 0 | 15 | 30 | 45 | 60 |
| | Feedstock gas ⇒ Gas sucked | | 0 | 3 | 6 | 8 | 10 | 0 | 5 | 8 | 11 | 13 |
| Dew point (under pressure) | Second supply gas | ° C. | −20 | −24 | −27 | −30 | −33 | −8 | −13 | −17 | −21 | −25 |
| Gas separation selectivity 1) | First gas separation membrane unit | — | 1.00 | 1.00 | 1.00 | 1.00 | 1.00 | 1.00 | 1.00 | 1.00 | 1.00 | 1.00 |
| | Second gas separation membrane unit | | 1.00 | 1.00 | 1.00 | 1.00 | 1.00 | 0.46 | 0.46 | 0.46 | 0.46 | 0.46 |
| | Third gas separation membrane unit | | 1.00 | 1.00 | 1.00 | 1.00 | 1.00 | 1.00 | 1.00 | 1.00 | 1.00 | 1.00 |

TABLE 3-continued

| | | | Comp. Ex. 3 | Ex. 3-1 | Ex. 3-2 | Ex. 3-3 | Ex. 3-4 | Comp. Ex. 4 | Ex. 4-1 | Ex. 4-2 | Ex. 4-3 | Ex. 4-4 |
|---|---|---|---|---|---|---|---|---|---|---|---|---|
| Amount of gas flow | First supply gas (F1) | $Nm^3/h$ | 342 | 330 | 321 | 314 | 309 | 393 | 371 | 353 | 339 | 329 |
| | Second supply gas (F2) | | 199 | 187 | 178 | 171 | 166 | 251 | 228 | 210 | 196 | 186 |
| | Third supply gas (F3) | | 143 | 143 | 143 | 143 | 143 | 142 | 142 | 143 | 143 | 143 |
| Amount of gas flow refluxed | Second permeate + Third retentate (F4) | | 142 | 130 | 121 | 114 | 109 | 193 | 171 | 153 | 139 | 129 |
| Reflux rate | (F4)/(F1) | % | 41 | 39 | 38 | 36 | 35 | 49 | 46 | 43 | 41 | 39 |
| CO2 concentration | First supply gas | mol % | 47 | 47 | 48 | 49 | 49 | 44 | 45 | 46 | 47 | 48 |
| | First permeate gas | | 88 | 88 | 88 | 88 | 88 | 88 | 88 | 88 | 88 | 88 |
| | First retentate gas | | 17 | 17 | 16 | 16 | 15 | 19 | 18 | 18 | 17 | 16 |
| | Second permeate gas | | 42 | 45 | 48 | 51 | 54 | 36 | 38 | 40 | 43 | 46 |
| | Third permeate gas | | 98 | 98 | 98 | 98 | 98 | 98 | 98 | 98 | 98 | 98 |
| | Third retentate gas | | 74 | 74 | 74 | 74 | 75 | 74 | 74 | 74 | 74 | 74 |
| Number of modules | First gas separation membrane unit | pc | 20 | 20 | 20 | 20 | 20 | 20 | 20 | 20 | 20 | 20 |
| | Second gas separation membrane unit | | 42 | 53 | 70 | 100 | 156 | 20 | 22 | 25 | 30 | 38 |
| | Third gas separation membrane unit | | 13 | 13 | 13 | 13 | 13 | 13 | 13 | 13 | 13 | 13 |
| | Total | | 75 | 86 | 103 | 133 | 189 | 53 | 55 | 58 | 63 | 71 |
| Product gas | CO2 concentration | | ≤50 ppmv | ≤50 ppmv | ≤50 ppmv | ≤50 ppmv | ≤50 ppmv | ≤50 ppmv | ≤50 ppmv | ≤50 ppmv | ≤50 ppmv | ≤50 ppmv |
| | CH4 recovery rate | % | 99.5 | 99.5 | 99.5 | 99.5 | 99.5 | 99.5 | 99.5 | 99.5 | 99.5 | 99.5 |

1) Relative value to gas separation selectivity of first gas separation membrane unit (at 40° C.)

From the results shown in Tables 2 and 3, it can be seen that the gas separation system of the present invention is capable of producing CHA with high purity enough to be liquefied from the feedstock gas containing carbon dioxide and CHA by a reduced the power for compression. In addition, in the gas separation system of the present invention, in which the separation selectivity of the second gas separation membrane unit at 40° C. is lower than the separation selectivity of the first gas separation membrane unit at 40° C., it is possible to reduce the number of gas separation membrane modules used in the second gas separation membrane unit while maintaining the purity of $CH_4$ to be recovered, the recovery rate and the power for compression, and it is found that it is possible to achieve both low power for compression and small area while maintaining high purity.

INDUSTRIAL APPLICABILITY

According to the present invention, high-purity $CH_4$ can be obtained from a feedstock gas containing $CO_2$ and $CH_4$ at low cost using separation membrane with a small area.

What is claimed is:

1. A gas separation system for producing a $CH_4$-enriched gas from a feedstock gas comprising $CO_2$ and $CH_4$, the gas separation system comprising a first gas separation membrane unit and a second gas separation membrane unit, wherein each of the first gas separation membrane unit and the second gas separation membrane unit includes at least a gas inlet, a permeate gas outlet and a retentate gas outlet, the gas separation system comprises:

a feedstock gas supply line connected to the gas inlet of the first gas separation membrane unit;

a compression part disposed in the feedstock gas supply line;

a first line connecting the retentate gas outlet of the first gas separation membrane unit and the gas inlet of the second gas separation membrane unit;

a second line connecting the permeate gas outlet of the second gas separation membrane unit and the feedstock gas supply line, and a cooling part for lowering an operating temperature of the second gas separation membrane unit, T2, below an operating temperature of the first gas separation membrane unit, T1, and wherein a gas permeation rate of the second gas separation membrane unit at 40° C., P2'CO2(40), is higher than a gas permeation rate of the first gas separation membrane unit at 40° C., P1'CO2(40).

2. The gas separation system according to claim 1, wherein a temperature of a gas supplied to the second gas separation membrane unit is 30° C. or less.

3. The gas separation system according to claim 1, wherein a temperature of the gas supplied to the second gas separation membrane unit is lower than a temperature of a gas supplied to the first gas separation membrane unit.

4. The gas separation system according to claim 1, wherein a difference between the operating temperatures T1 and T2, T1-T2, is 10° C. or more.

5. The gas separation system according to claim 1, wherein during operation of the gas separation system, a gas separation membrane included in the second gas separation membrane unit has a separation selectivity $P_2'CO_2/P_2'CH_4$ of 15 or more and 3000 or less, and a $CO_2$ permeation rate $P_2'CO_2$ of $3\times10^{-5}$ $cm^3$ (STP)/$cm^2$·sec·cmHg or more and $80\times10^{-5}$ $cm^3$ (STP)/$cm^2$·sec·cmHg or less.

6. The gas separation system according to claim 1, wherein the cooling part is disposed in the first line.

7. The gas separation system according to claim 1, wherein a proportion of an amount of a gas flow refluxed to the first gas separation membrane unit in an amount of a gas flow supplied to the first gas separation membrane unit is 10 to 60%.

8. The gas separation system according to claim 1, further comprising a third gas separation membrane unit, wherein the third gas separation membrane unit comprises at least a gas inlet, a permeate gas outlet and a retentate gas outlet, and the gas separation system comprises:

a third line connecting the permeate gas outlet of the first gas separation membrane unit and the gas inlet of the third gas separation membrane unit, and a fourth line connecting the retentate gas outlet of the third gas separation membrane unit and the feedstock gas supply line.

9. The gas separation system according to claim 1, comprising a liquefaction device for further cooling and liquefying a retentate gas of the second gas separation membrane unit.

10. A gas separation system for producing a $CH_4$-enriched gas from a feedstock gas comprising $CO_2$ and $CH_4$, the gas separation system comprising a first gas separation membrane unit and a second gas separation membrane unit, wherein each of the first gas separation membrane unit and the second gas separation membrane unit includes at least a gas inlet, a permeate gas outlet and a retentate gas outlet, the gas separation system comprises:

a feedstock gas supply line connected to the gas inlet of the first gas separation membrane unit;

a compression part disposed in the feedstock gas supply line;

a first line connecting the retentate gas outlet of the first gas separation membrane unit and the gas inlet of the second gas separation membrane unit;

a second line connecting the permeate gas outlet of the second gas separation membrane unit and the feedstock gas supply line, and a cooling part for lowering an operating temperature of the second gas separation membrane unit, T2, below an operating temperature of the first gas separation membrane unit, T1, and wherein a carbon dioxide gas permeation rate of the second gas separation membrane unit at the operating temperature T2, P1'CO2(T2), is higher than a carbon dioxide gas permeation rate of the first gas separation membrane unit at the operating temperature T1, P1'CO2(T1).

11. A gas separation system for producing a $CH_4$-enriched gas from a feedstock gas comprising $CO_2$ and $CH_4$, the gas separation system comprising a first gas separation membrane unit and a second gas separation membrane unit, wherein each of the first gas separation membrane unit and the second gas separation membrane unit includes at least a gas inlet, a permeate gas outlet and a retentate gas outlet, the gas separation system comprises:

a feedstock gas supply line connected to the gas inlet of the first gas separation membrane unit;

a compression part disposed in the feedstock gas supply line;

a first line connecting the retentate gas outlet of the first gas separation membrane unit and the gas inlet of the second gas separation membrane unit;

a second line connecting the permeate gas outlet of the second gas separation membrane unit and the feedstock gas supply line, and a cooling part for lowering an operating temperature of the second gas separation membrane unit, T2, below an operating temperature of the first gas separation membrane unit, T1, and the gas separation system comprises a heating part for heating the feedstock gas supplied to the first gas separation membrane unit, the heating part being provided in the feedstock gas supply line.

12. A gas separation system for producing a $CH_4$-enriched gas from a feedstock gas comprising $CO_2$ and $CH_4$, the gas separation system comprises a first gas separation membrane unit, a second gas separation membrane unit, and a third gas separation membrane unit, wherein each of the first gas separation membrane unit and the second gas separation membrane unit includes at least a gas inlet, a permeate gas outlet and a retentate gas outlet, the gas separation system comprises:

a feedstock gas supply line connected to the gas inlet of the first gas separation membrane unit;

a compression part disposed in the feedstock gas supply line;

a first line connecting the retentate gas outlet of the first gas separation membrane unit and the gas inlet of the second gas separation membrane unit;

a second line connecting the permeate gas outlet of the second gas separation membrane unit and the feedstock gas supply line, and a cooling part for lowering an operating temperature of the second gas separation membrane unit, T2, below an operating temperature of the first gas separation membrane unit, T1, the third gas separation membrane unit comprises at least a gas inlet, a permeate gas outlet and a retentate gas outlet, the gas separation system comprises:

a third line connecting the permeate gas outlet of the first gas separation membrane unit and the gas inlet of the third gas separation membrane unit, and a fourth line connecting the retentate gas outlet of the third gas separation membrane unit and the feedstock gas supply line, wherein the operating temperature of the second gas separation membrane unit is lower than an operating temperature of the third gas separation membrane unit.

13. A gas separation system for producing a $CH_4$-enriched gas from a feedstock gas comprising $CO_2$ and $CH_4$, the gas separation system comprising a first gas separation membrane unit and a second gas separation membrane unit, wherein each of the first gas separation membrane unit and the second gas separation membrane unit includes at least a gas inlet, a permeate gas outlet and a retentate gas outlet, the gas separation system comprises:

a feedstock gas supply line connected to the gas inlet of the first gas separation membrane unit;

a compression part disposed in the feedstock gas supply line;

a first line connecting the retentate gas outlet of the first gas separation membrane unit and the gas inlet of the second gas separation membrane unit;

a second line connecting the permeate gas outlet of the second gas separation membrane unit and the feedstock gas supply line, and a cooling part for lowering an operating temperature of the second gas separation membrane unit, T2, below an operating temperature of the first gas separation membrane unit, T1, wherein a cooled retentate gas of the second gas separation membrane unit is used to lower the operating temperature of the second gas separation membrane unit.

14. A method for producing a $CH_4$-enriched gas, comprising supplying a feedstock gas comprising at least $CO_2$ and $CH_4$ to a gas separation system, wherein the gas separation system comprises at least a first gas separation membrane unit and a second gas separation membrane unit, each of the first gas separation membrane unit and the second gas separation membrane unit includes at least a gas inlet, a permeate gas outlet, and a retentate gas outlet, the gas separation system comprises:

a feedstock gas supply line connected to the gas inlet of the first gas separation membrane unit;

a compression part disposed in the feedstock gas supply line;

a first line connecting the retentate gas outlet of the first gas separation membrane unit and the gas inlet of the second gas separation membrane unit;

a second line connecting the permeate gas outlet of the second gas separation membrane unit and the feedstock gas supply line, and a cooling part for lowering an operating temperature of the second gas separation membrane unit below an operating temperature of the first gas separation membrane unit, wherein a gas permeation rate of the second gas separation membrane unit at 40° C., $P_2'CO_2^{(40)}$, is higher than a gas permeation rate of the first gas separation membrane unit at 40° C., $P_1'CO_2^{(40)}$.

* * * * *